US011000579B2

(12) United States Patent
Jenkins et al.

(10) Patent No.: US 11,000,579 B2
(45) Date of Patent: May 11, 2021

(54) **RECOMBINANT *EIMERIA MAXIMA* PROTEIN DELIVERED AS NANOPARTICLES**

(71) Applicants: The United States of America, as represented by the Secretary of Agriculture, Washington, DC (US); Board of Trustees Southern Illinois University, Carbondale, IL (US)

(72) Inventors: Mark C. Jenkins, Davidsonville, MD (US); Vjollca Konjufca, Carbondale, IL (US)

(73) Assignees: The United States of America, as represented by The Secretary of Agriculture, Washington, DC (US); Board of Trustees of Souther Illinois University, Springfield, IL (US)

( * ) Notice: Subject to any disclaimer, the term of this patent is extended or adjusted under 35 U.S.C. 154(b) by 0 days.

(21) Appl. No.: 16/245,773

(22) Filed: Jan. 11, 2019

(65) Prior Publication Data

US 2019/0216911 A1   Jul. 18, 2019

Related U.S. Application Data

(60) Provisional application No. 62/616,503, filed on Jan. 12, 2018.

(51) Int. Cl.
*A61K 39/012* (2006.01)
*A61P 33/10* (2006.01)
*A61K 39/00* (2006.01)

(52) U.S. Cl.
CPC ............ *A61K 39/012* (2013.01); *A61P 33/10* (2018.01); *A61K 2039/542* (2013.01); *A61K 2039/543* (2013.01); *A61K 2039/552* (2013.01); *A61K 2039/60* (2013.01)

(58) Field of Classification Search
None
See application file for complete search history.

(56) References Cited

U.S. PATENT DOCUMENTS

2013/0216569 A1   8/2013   Blake et al.

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Blake, Damer P. et al., "Genetic Mapping Identifies Novel Highly Protective Antigens for an Apicomplexan Parasite," PLoS Pathogens, (2011), 7(2):1-13.
Jenkins, M.C. et al., "Characterization of the Eimeria Maxima Sporozoite Surface Protein IMP1, Veterinary Parasitology," (2015), 211:146-152.

* cited by examiner

*Primary Examiner* — Robert A Zeman
(74) *Attorney, Agent, or Firm* — John D. Fado; Mark D. McNemar

(57) ABSTRACT

Provided herein are immunogenic compositions containing recombinant proteins capable of presenting all, or antigenic portions of, the *Eimeria maxima*, *Eimeria tenella*, and *Eimeria acervulina* IMP1 protein in developing active immunity to, and control of, coccidiosis. Also provided are methodologies of using the immunogenic compositions for administration to poultry and other animals in the control of coccidiosis. Nanoparticle-conjugated rIMP1 immunogenic compositions and methods of making and using them are provided.

7 Claims, 5 Drawing Sheets
(2 of 5 Drawing Sheet(s) Filed in Color)
Specification includes a Sequence Listing.

```
                        SEQUENCE LISTING

<160> NUMBER OF SEQ ID NOS: 6

<210> SEQ ID NO 1
<211> LENGTH: 1254
<212> TYPE: DNA
<213> ORGANISM: Eimeria maxima

<400> SEQUENCE: 1 atgggggtt  ctcatcatca  tcatcatcat  ggtatggcta  gcatgactgg  tggacagcaa      60
atgggtcggg  atctgtacga  cgatgacgat  aaggatcgat  ggggatccga  gctcgagatg     120
ggggccgctt  gcgggaaatc  gcagcgcgcc  gccgccgctg  ttgaaccccc  cctttctacc     180
gcggagaagg  cagaagcagc  agcagtagca  gcagcagaac  atagccagaa  agcagaggaa     240
gcagcagaag  ttgctgctgc  ttgtgcgacg  aaagcttccg  cagaggctgc  tctccttaca     300
ggggtcgagc  caggggcaga  gcctgctgct  gaggcagaag  aggccccaaa  acaaaatgaa     360
atagaagagc  agcaaacaac  aacaacaccc  gcacaaacgc  atgcaacaga  agagcagcca     420
gcagctcctc  ctgttgttcc  cttgagcgat  gcagatgcac  aagttcttgc  tgcagcagaa     480
gcagcaaagc  aggaagcagc  tagtagcaat  atgcctaggg  cgtatttgtt  ttatgcatgc     540
gaactcaatg  aaggatcctt  aatgatgcaa  tggactacta  cacaaataac  ggaagaagat     600
atgcatgcaa  agaatctaat  tcttcttgcc  tcctttttc   ctgctaaaca  taaaactgtt     660
tctaagagca  aacttacaca  aaatggaggt  attacctact  tcctgcagga  gatgaagtac     720
aagtgggagg  tttggagcaa  agtgcagaga  caggcatatt  atcagggttg  gataaaattc     780
gtcaaagcag  cagatgagat  ggaggcgtca  ttcaccttac  accactttgc  tgctcctgcg     840
ccacccgcca  aactttttctt  actgcataca  ggacctattg  agaataaggt  actgcctgct     900
aaggaagaag  aaccattcaa  tgtctccgtc  ttcggtcttg  ctgcggtgac  gccgccgtcg     960
cctccttaca  agccaggagc  gaacattaca  ccaaagagat  tcggcgaaat  cgccaccgga    1020
gcaggtgggg  cttacatgca  gctttcccgc  agaggcggtg  atgcagcatt  tgatgagaaa    1080
gaagttcaga  agtggctggc  ggctgacggt  cttcaaatga  aaaagggaga  aggaattaca    1140
ttggatgcag  caggcggtta  tgaacgaaga  tctgagaaaa  agggggcga   tgctgcagct    1200 gcaactgcag  ccgtagaagc  agagcccact  aaagtgtcgc  aagattgagg  tacc          1254

<210> SEQ ID NO 2
<211> LENGTH: 415
<212> TYPE: PRT
<213> ORGANISM: Eimeria maxima

<400> SEQUENCE: 2

Met Gly Gly Ser His His His His His Gly Met Ala Ser Met Thr
1               5                   10                  15

Gly Gly Gln Gln Met Gly Arg Thr Leu Tyr Asp Asp Asp Lys Asp
                20                  25                  30

Arg Trp Gly Ser Glu Leu Glu Met Gly Ala Ala Cys Gly Lys Ser Gln
        35                  40                  45
```

-continued

Arg Ala Ala Ala Val Glu Pro Pro Leu Ser Thr Ala Glu Lys Ala
    50              55                  60

Glu Ala Ala Ala Val Ala Ala Glu His Ser Gln Lys Ala Glu Glu
65              70              75                      80

Ala Ala Glu Val Ala Ala Ala Cys Ala Thr Lys Ala Ser Ala Glu Ala
                85              90              95

Ala Leu Leu Thr Gly Val Glu Pro Gly Ala Glu Pro Ala Ala Glu Ala
            100             105             110

Glu Glu Ala Pro Lys Gln Asn Glu Ile Glu Glu Gln Gln Thr Thr Thr
        115             120             125

Thr Pro Ala Gln Thr His Ala Thr Glu Glu Gln Pro Ala Ala Pro Pro
        130             135             140

Val Val Pro Leu Ser Asp Ala Asp Ala Gln Val Leu Ala Ala Ala Glu
145             150             155             160

Ala Ala Lys Gln Glu Ala Ala Ser Ser Asn Met Pro Arg Ala Tyr Leu
            165             170             175

Phe Tyr Ala Cys Glu Leu Asn Glu Gly Ser Leu Met Met Gln Trp Thr
            180             185             190

Thr Thr Gln Ile Thr Glu Glu Asp Met His Ala Lys Asn Leu Ile Leu
        195             200             205

Leu Ala Ser Phe Phe Pro Ala Lys His Lys Thr Val Ser Lys Ser Lys
    210             215             220

Leu Thr Gln Asn Gly Gly Ile Thr Tyr Phe Leu Gln Glu Met Lys Tyr
225             230             235             240

Lys Trp Glu Val Trp Ser Lys Val Gln Arg Gln Ala Tyr Tyr Gln Gly
            245             250             255

Trp Ile Lys Phe Val Lys Ala Ala Asp Glu Met Glu Ala Ser Phe Thr
            260             265             270

Leu His His Phe Ala Ala Pro Ala Pro Pro Ala Lys Leu Phe Leu Leu
        275             280             285

His Thr Gly Pro Ile Glu Asn Lys Val Leu Pro Ala Lys Glu Glu Glu
        290             295             300

Pro Phe Asn Val Ser Val Phe Gly Leu Ala Ala Val Thr Pro Pro Ser
305             310             315             320

Pro Pro Tyr Lys Pro Gly Ala Asn Ile Thr Pro Lys Arg Phe Gly Glu
            325             330             335

Ile Ala Thr Gly Ala Gly Gly Ala Tyr Met Gln Leu Ser Arg Arg Gly
            340             345             350

Gly Asp Ala Ala Phe Asp Glu Lys Glu Val Gln Lys Trp Leu Ala Ala
        355             360             365

Asp Gly Leu Gln Met Lys Lys Gly Glu Gly Ile Thr Leu Asp Ala Ala
        370             375             380

Gly Gly Tyr Glu Arg Arg Ser Glu Lys Lys Gly Gly Asp Ala Ala Ala
385             390             395             400

Ala Thr Ala Ala Val Glu Ala Glu Pro Thr Lys Val Ser Gln Asp
            405             410             415

<210> SEQ ID NO 3
<211> LENGTH: 1323
<212> TYPE: PRT
<213> ORGANISM: Eimeria tenella -continued

```
<400> SEQUENCE: 3

Ala Thr Gly Gly Gly Gly Thr Thr Cys Thr Cys Ala Thr Cys
1               5                   10                  15
Ala Thr Cys Ala Thr Cys Ala Thr Cys Ala Thr Cys Ala Thr Gly Gly
            20                  25                  30
Thr Ala Thr Gly Gly Cys Thr Ala Gly Cys Ala Thr Gly Ala Cys Thr
            35                  40                  45
Gly Gly Thr Gly Gly Ala Cys Ala Gly Cys Ala Ala Ala Thr Gly Gly
            50                  55                  60
Gly Thr Cys Gly Gly Ala Thr Cys Thr Gly Thr Ala Cys Gly Ala
65                  70                  75                  80
Cys Gly Ala Thr Gly Ala Cys Gly Ala Thr Ala Ala Gly Gly Ala Thr
            85                  90                  95
Cys Cys Gly Ala Gly Cys Thr Cys Gly Ala Gly Ala Thr Cys Thr Gly
            100                 105                 110
Cys Ala Gly Cys Thr Gly Gly Thr Ala Cys Cys Ala Thr Gly Gly Gly
            115                 120                 125
Thr Gly Gly Cys Gly Gly Thr Gly Cys Gly Gly Cys Ala Ala Gly
            130                 135                 140
Ala Gly Cys Cys Gly Thr Gly Gly Ala Cys Cys Gly Cys Gly Gly
145                 150                 155                 160
Cys Gly Gly Cys Gly Gly Cys Gly Gly Ala Ala Cys Cys Gly Cys Cys
            165                 170                 175
Gly Gly Thr Gly Ala Gly Cys Gly Cys Gly Gly Cys Gly Gly Ala Cys
            180                 185                 190
Ala Ala Ala Gly Cys Gly Gly Cys Gly Gly Ala Gly Gly Cys Gly Gly
            195                 200                 205
Cys Gly Gly Cys Gly Ala Gly Cys Gly Cys Gly Gly Cys Gly Ala Gly
            210                 215                 220
Cys Cys Ala Gly Gly Cys Gly Gly Ala Gly Ala Ala Ala Gly Cys Gly
225                 230                 235                 240
Cys Ala Ala Gly Ala Ala Gly Cys Gly Gly Cys Thr Gly Cys Thr Gly
            245                 250                 255
Cys Gly Gly Cys Thr Gly Cys Thr Gly Cys Gly Gly Cys Gly Gly Cys
            260                 265                 270
Gly Gly Cys Gly Ala Ala Cys Gly Gly Thr Gly Cys Gly Gly Cys Thr
            275                 280                 285
Gly Cys Gly Gly Cys Gly Gly Cys Gly Gly Cys Gly Cys Thr Gly Ala
            290                 295                 300
Cys Cys Gly Gly Cys Gly Ala Ala Gly Ala Thr Cys Gly Thr Ala Gly
305                 310                 315                 320
Cys Gly Ala Gly Cys Gly Thr Gly Ala Cys Cys Gly Gly Cys Gly
            325                 330                 335
Ala Ala Cys Gly Cys Gly Ala Cys Gly Ala Cys Gly Gly Thr Ala
            340                 345                 350
Ala Ala Gly Ala Thr Ala Cys Cys Ala Ala Cys Cys Cys Gly Ala Cys
            355                 360                 365
Cys Ala Ala Cys Cys Gly Ala Cys Cys Ala Cys Cys Gly Cys Gly
            370                 375                 380
Gly Ala Gly Cys Ala Gly Cys Ala Ala Cys Ala Gly Cys Ala Ala Cys
385                 390                 395                 400
Ala Gly Gly Ala Gly Cys Ala Gly Gly Ala Ala Cys Ala Ala Cys Ala
            405                 410                 415
```

-continued

```
Gly Cys Ala Ala Cys Ala Gly Gly Ala Gly Cys Ala Ala Cys Ala Gly
                420                 425                 430
Cys Ala Ala Cys Ala Ala Gly Ala Gly Cys Ala Gly Cys Ala Ala Cys
                435                 440                 445
Ala Gly Cys Ala Ala Gly Ala Gly Cys Ala Ala Cys Ala Gly Cys Ala
450                 455                 460
Ala Cys Ala Ala Gly Ala Ala Cys Ala Gly Cys Ala Ala Cys Ala Gly
465                 470                 475                 480
Cys Ala Gly Gly Ala Gly Cys Ala Ala Cys Ala Gly Cys Ala Gly Gly
                485                 490                 495
Gly Thr Gly Cys Gly Gly Cys Gly Gly Cys Gly Gly Cys Gly Cys Ala
        500                 505                 510
Gly Cys Ala Ala Cys Cys Gly Gly Cys Gly Ala Gly Cys Cys Cys Gly
        515                 520                 525
Gly Thr Gly Gly Thr Thr Gly Cys Gly Cys Thr Gly Ala Gly Cys Gly
        530                 535                 540
Cys Gly Gly Cys Gly Gly Ala Cys Gly Cys Gly Gly Ala Ala Cys Thr
545                 550                 555                 560
Gly Cys Thr Gly Gly Cys Gly Gly Cys Gly Gly Cys Gly Cys Ala Ala
                565                 570                 575
Cys Ala Gly Cys Ala Gly Gly Cys Thr Gly Cys Cys Gly Cys Gly Gly
                580                 585                 590
Cys Gly Gly Cys Gly Gly Cys Gly Gly Cys Gly Gly Thr Ala Gly Gly
                595                 600                 605
Cys Ala Ala Cys Gly Cys Gly Ala Ala Cys Cys Thr Gly Cys Cys Gly
                610                 615                 620
Cys Ala Cys Gly Cys Gly Thr Ala Cys Cys Thr Gly Thr Thr Cys Thr
625                 630                 635                 640
Ala Thr Gly Cys Gly Gly Cys Gly Gly Ala Gly Cys Thr Gly Ala Ala
                645                 650                 655
Cys Gly Ala Ala Gly Gly Cys Ala Gly Cys Cys Thr Gly Ala Thr Cys
                660                 665                 670
Cys Thr Gly Cys Ala Gly Thr Gly Gly Ala Cys Cys Gly Cys Gly Gly
                675                 680                 685
Cys Gly Gly Cys Gly Ala Thr Gly Cys Ala Ala Cys Ala Gly Cys Ala
                690                 695                 700
Ala Gly Ala Ala Ala Thr Gly Cys Ala Gly Gly Ala Thr Ala Ala Gly
705                 710                 715                 720
Ala Ala Ala Cys Thr Gly Cys Thr Gly Cys Thr Gly Cys Thr Gly Gly
                725                 730                 735
Cys Gly Ala Gly Cys Thr Thr Thr Gly Thr Gly Cys Cys Gly Cys Cys
                740                 745                 750
Gly Ala Ala Gly Thr Ala Cys Ala Ala Ala Cys Cys Gly Thr Thr
                755                 760                 765
Ala Cys Cys Ala Ala Gly Ala Gly Cys Ala Ala Cys Thr Gly Cys
                770                 775                 780
Ala Gly Cys Ala Ala Ala Cys Gly Gly Thr Gly Gly Cys Ala Thr
785                 790                 795                 800
Cys Ala Cys Cys Thr Thr Thr Cys Thr Gly Cys Thr Gly Cys Ala Gly
                805                 810                 815
Gly Ala Gly Ala Thr Gly Ala Ala Gly Thr Ala Cys Ala Ala Ala Thr
                820                 825                 830
```

-continued

```
Gly Gly Gly Ala Cys Ala Thr Thr Gly Gly Ala Ala Cys Ala Ala
            835                 840                 845
Gly Gly Cys Gly Cys Ala Gly Cys Gly Thr Cys Ala Ala Gly Cys Gly
            850                 855                 860
Thr Ala Thr Thr Thr Cys Cys Ala Gly Gly Thr Thr Gly Gly Gly
865                 870                 875                 880
Cys Gly Ala Ala Gly Thr Thr Cys Thr Gly Ala Ala Gly Cys
                885                 890                 895
Gly Gly Cys Gly Gly Ala Thr Gly Ala Gly Ala Thr Gly Ala Ala
            900                 905                 910
Gly Cys Gly Ala Gly Cys Cys Thr Gly Cys Thr Gly Cys Thr Gly Cys
            915                 920                 925
Ala Thr Cys Cys Gly Thr Thr Thr Gly Ala Ala Cys Thr Gly Cys Cys
            930                 935                 940
Gly Gly Cys Thr Cys Cys Gly Cys Cys Gly Gly Cys Gly Ala Cys Cys
945                 950                 955                 960
Gly Thr Gly Thr Thr Thr Cys Thr Gly Cys Thr Gly Cys Ala Cys Ala
            965                 970                 975
Cys Cys Gly Gly Thr Cys Cys Gly Ala Thr Thr Gly Ala Ala Ala Ala
            980                 985                 990
Cys Ala Ala Gly Gly Thr Gly Gly Thr Thr Cys Cys Gly Gly Thr Thr
            995                1000                1005
Ala Ala Ala Cys Thr Gly Gly Gly Cys Gly Ala Gly Cys Cys Gly
            1010                1015                1020
Ala Thr Cys Gly Gly Cys Ala Thr Thr Ala Gly Cys Ala Thr Gly
            1025                1030                1035
Thr Thr Cys Gly Gly Cys Thr Thr Thr Gly Cys Gly Gly Cys Gly
            1040                1045                1050
Gly Thr Gly Gly Cys Thr Cys Gly Cys Cys Gly Cys Cys Gly
            1055                1060                1065
Gly Cys Gly Cys Cys Gly Thr Ala Cys Ala Ala Gly Gly Cys Gly
            1070                1075                1080
Gly Gly Thr Gly Cys Gly Ala Ala Cys Ala Thr Cys Ala Cys Cys
            1085                1090                1095
Cys Cys Gly Ala Ala Ala Cys Gly Thr Thr Thr Gly Gly Thr
            1100                1105                1110
Gly Ala Ala Cys Thr Gly Gly Cys Gly Ala Cys Cys Cys Ala Gly
            1115                1120                1125
Gly Cys Gly Gly Gly Thr Gly Cys Gly Cys Gly Thr Ala Thr
            1130                1135                1140
Ala Thr Thr Cys Ala Ala Cys Thr Gly Ala Gly Cys Cys Gly Thr
            1145                1150                1155
Cys Gly Thr Gly Gly Thr Gly Cys Gly Ala Cys Gly Cys Gly
            1160                1165                1170
Gly Cys Gly Thr Thr Thr Ala Gly Cys Gly Ala Gly Gly Cys Gly
            1175                1180                1185
Gly Ala Thr Gly Thr Gly Gly Thr Thr Ala Ala Thr Gly Gly
            1190                1195                1200
Cys Thr Gly Gly Cys Gly Gly Ala Gly Gly Ala Cys Gly Gly Thr
            1205                1210                1215
Cys Thr Gly Gly Ala Ala Ala Thr Cys Cys Ala Gly Cys Ala Gly
            1220                1225                1230
```

-continued

```
Gly Gly Thr Ala Ala Cys Gly Gly Cys Ala Thr Thr Ala Cys Cys
    1235                1240                1245

Cys Thr Gly Gly Ala Cys Ala Gly Cys Ala Cys Cys Gly Gly Cys
    1250                1255                1260

Gly Cys Gly Thr Ala Thr Gly Ala Gly Cys Gly Thr Cys Gly Thr
    1265                1270                1275

Ala Gly Cys Gly Ala Thr Ala Ala Gly Ala Ala Ala Gly Gly Thr
    1280                1285                1290

Gly Gly Cys Ala Ala Cys Gly Thr Thr Gly Cys Gly Gly Cys Gly
    1295                1300                1305

Gly Cys Gly Ala Cys Cys Thr Ala Ala Gly Ala Ala Thr Thr Cys
    1310                1315                1320
```

<210> SEQ ID NO 4
<211> LENGTH: 438
<212> TYPE: PRT
<213> ORGANISM: Eimeria tenella

<400> SEQUENCE: 4

```
Met Gly Gly Ser His His His His His Gly Met Ala Ser Met Thr
1                5                  10                 15

Gly Gly Gln Gln Met Gly Arg Asp Leu Tyr Asp Asp Asp Lys Asp
                20                 25                 30

Pro Ser Ser Arg Ser Ala Ala Gly Thr Met Gly Gly Ala Cys Gly Lys
                35                 40                 45

Ser Arg Gly Thr Ala Ala Ala Glu Pro Pro Val Ser Ala Ala Asp
            50                 55                 60

Lys Ala Ala Glu Ala Ala Ala Ser Ala Ala Ser Gln Ala Glu Lys Ala
65                  70                 75                 80

Gln Glu Ala Ala Ala Ala Ala Ala Ala Ala Ala Asn Gly Ala Ala
                85                 90                 95

Ala Ala Ala Ala Leu Thr Gly Glu Asp Arg Ser Glu Arg Glu Pro Ala
                100                105                110

Asn Ala Ser Asp Gly Lys Asp Thr Asn Pro Thr Asn Pro Thr Thr Ala
                115                120                125

Glu Gln Gln Gln Gln Gln Glu Gln Gln Gln Gln Gln Glu Gln Gln
                130                135                140

Gln Gln Glu Gln Gln Gln Gln Glu Gln Gln Gln Gln Glu Gln Gln Gln
145                150                155                160

Gln Glu Gln Gln Gln Gly Ala Ala Ala Ala Gln Gln Pro Ala Ser Pro
                165                170                175

Val Val Ala Leu Ser Ala Ala Asp Ala Glu Leu Leu Ala Ala Ala Gln
                180                185                190

Gln Gln Ala Ala Ala Ala Ala Ala Gly Ser Asn Ala Asn Leu Pro
                195                200                205

His Ala Tyr Leu Phe Tyr Ala Ala Glu Leu Asn Glu Gly Ser Leu Ile
                210                215                220

Leu Gln Trp Thr Ala Ala Ala Met Gln Gln Gln Glu Met Gln Asp Lys
225                230                235                240

Lys Leu Leu Leu Leu Ala Ser Phe Val Pro Pro Lys Tyr Lys Thr Val
                245                250                255

Thr Lys Ser Lys Leu Gln Gln Asn Gly Gly Ile Thr Phe Leu Leu Gln
                260                265                270

Glu Met Lys Tyr Lys Trp Asp Ile Trp Asn Lys Ala Gln Arg Gln Ala
                275                280                285
```

```
Tyr Phe Gln Gly Trp Ala Lys Phe Leu Lys Ala Ala Asp Glu Met Glu
    290                 295                 300

Ala Ser Leu Leu Leu His Pro Phe Glu Leu Pro Ala Pro Pro Ala Thr
305                 310                 315                 320

Val Phe Leu Leu His Thr Gly Pro Ile Glu Asn Lys Val Val Pro Val
                325                 330                 335

Lys Leu Gly Glu Pro Ile Gly Ile Ser Met Phe Gly Phe Ala Ala Val
            340                 345                 350

Ala Pro Pro Ala Pro Tyr Lys Ala Gly Ala Asn Ile Thr Pro Lys
        355                 360                 365

Arg Phe Gly Leu Ala Thr Gln Ala Gly Ala Tyr Ile Gln Leu
370                 375                 380

Ser Arg Arg Gly Gly Asp Ala Ala Phe Ser Glu Ala Asp Val Val Lys
385                 390                 395                 400

Trp Leu Ala Glu Asp Gly Leu Glu Ile Gln Gln Gly Asn Gly Ile Thr
                405                 410                 415

Leu Asp Ser Thr Gly Ala Tyr Glu Arg Arg Ser Asp Lys Lys Gly Gly
            420                 425                 430

Asn Val Ala Ala Ala Thr
            435

<210> SEQ ID NO 5
<211> LENGTH: 1224
<212> TYPE: PRT
<213> ORGANISM: Eimeria acervulina

<400> SEQUENCE: 5

Ala Thr Gly Gly Gly Gly Gly Thr Thr Cys Thr Cys Ala Thr Cys
1               5                   10                  15

Ala Thr Cys Ala Thr Cys Ala Thr Cys Ala Thr Cys Ala Thr Gly Gly
                20                  25                  30

Thr Ala Thr Gly Gly Cys Thr Ala Gly Cys Ala Thr Gly Ala Cys Thr
            35                  40                  45

Gly Gly Thr Gly Gly Ala Cys Ala Gly Cys Ala Ala Ala Thr Gly Gly
        50                  55                  60

Gly Thr Cys Gly Gly Gly Ala Thr Cys Thr Gly Thr Ala Cys Gly Ala
65                  70                  75                  80

Cys Gly Ala Thr Gly Ala Cys Gly Ala Thr Ala Ala Gly Gly Ala Thr
                85                  90                  95

Cys Gly Ala Thr Gly Gly Gly Ala Thr Cys Cys Gly Ala Gly Cys Thr
            100                 105                 110

Cys Gly Ala Gly Ala Thr Cys Thr Gly Gly Gly Cys Ala Thr Gly Cys
        115                 120                 125

Thr Thr Gly Cys Ala Thr Gly Ala Ala Ala Thr Cys Cys Cys Ala Cys
    130                 135                 140

Gly Gly Cys Gly Cys Cys Gly Cys Cys Ala Cys Gly Ala Cys Gly Gly
145                 150                 155                 160

Cys Thr Gly Thr Gly Gly Cys Ala Cys Cys Cys Gly Cys Ala Gly Gly
                165                 170                 175

Gly Thr Cys Cys Ala Cys Ala Gly Cys Thr Gly Ala Gly Ala Ala Gly
            180                 185                 190

Gly Cys Ala Gly Cys Ala Gly Ala Cys Gly Ala Gly Cys Ala Gly
        195                 200                 205

Cys Ala Gly Cys Ala Gly Cys Ala Gly Ala Gly Ala Ala Cys Ala
    210                 215                 220
```

-continued

```
Cys Ala Gly Cys Cys Ala Cys Ala Ala Ala Gly Cys Gly Cys Ala Gly
225                 230                 235                 240
Gly Ala Ala Gly Cys Ala Gly Cys Ala Gly Ala Gly Ala Cys Cys Gly
                245                 250                 255
Cys Thr Gly Cys Thr Gly Cys Thr Thr Gly Thr Gly Cys Thr Ala Gly
            260                 265                 270
Gly Cys Gly Gly Gly Cys Ala Thr Gly Thr Gly Cys Ala Gly Ala Ala
        275                 280                 285
Gly Cys Thr Gly Cys Thr Thr Cys Gly Cys Thr Cys Ala Cys Cys Gly
    290                 295                 300

Gly Gly Ala Gly Ala Gly Gly Gly Thr Cys Thr Gly Gly Thr Gly Ala
305                 310                 315                 320
Gly Gly Cys Thr Gly Cys Thr Gly Cys Ala Ala Thr Gly Cys Ala Ala
                325                 330                 335
Gly Gly Gly Gly Ala Cys Cys Cys Thr Ala Ala Gly Gly Thr Gly Gly
            340                 345                 350

Ala Cys Gly Ala Ala Ala Cys Ala Gly Ala Ala Gly Ala Ala Cys Ala
        355                 360                 365

Ala Cys Ala Ala Ala Thr Ala Ala Cys Gly Ala Cys Ala Ala Cys Thr
    370                 375                 380

Cys Cys Ala Gly Cys Ala Cys Ala Ala Ala Cys Gly Cys Ala Cys Gly
385                 390                 395                 400

Cys Ala Ala Cys Gly Gly Ala Ala Gly Ala Ala Cys Cys Cys Cys Ala
                405                 410                 415
Gly Gly Cys Gly Thr Cys Ala Gly Cys Thr Gly Thr Cys Gly Thr Thr
            420                 425                 430

Cys Cys Cys Cys Thr Gly Ala Gly Cys Gly Ala Thr Gly Cys Gly Gly
        435                 440                 445

Ala Cys Gly Cys Ala Cys Ala Gly Cys Thr Cys Thr Thr Gly Gly Cys
    450                 455                 460

Thr Gly Cys Ala Gly Cys Gly Gly Ala Gly Ala Ala Gly Cys Ala Gly
465                 470                 475                 480

Gly Cys Ala Gly Cys Ala Gly Cys Ala Ala Ala Gly Cys Ala Gly Cys
                485                 490                 495

Ala Gly Cys Ala Ala Gly Gly Gly Gly Gly Ala Thr Cys Thr Ala Ala
            500                 505                 510

Thr Ala Cys Ala Cys Cys Thr Cys Ala Cys Gly Cys Gly Thr Ala Thr
        515                 520                 525

Thr Thr Gly Thr Thr Cys Thr Ala Thr Gly Cys Cys Ala Cys Thr Gly
    530                 535                 540

Ala Ala Cys Thr Ala Ala Ala Thr Gly Ala Gly Gly Gly Thr Thr Cys
545                 550                 555                 560

Thr Cys Thr Ala Ala Thr Thr Ala Thr Gly Cys Ala Gly Thr Gly Gly
                565                 570                 575

Ala Cys Thr Cys Cys Ala Ala Cys Ala Cys Ala Ala Ala Thr Gly Ala
            580                 585                 590

Gly Cys Gly Ala Gly Gly Ala Ala Gly Ala Thr Ala Thr Gly Cys Ala
        595                 600                 605

Thr Gly Cys Ala Ala Ala Gly Ala Ala Cys Cys Thr Gly Cys Thr Gly
    610                 615                 620

Cys Thr Cys Cys Thr Cys Gly Cys Cys Thr Cys Cys Thr Thr Cys Ala
625                 630                 635                 640
```

```
Cys Thr Cys Cys Thr Gly Cys Cys Ala Ala Gly Cys Ala Cys Ala Ala
                645                 650                 655

Ala Ala Cys Cys Gly Thr Cys Thr Cys Thr Ala Gly Ala Gly Cys
        660                 665                 670

Ala Ala Ala Cys Thr Cys Ala Cys Ala Cys Ala Ala Ala Thr Gly
            675                 680                 685

Gly Ala Gly Gly Cys Gly Thr Thr Ala Cys Cys Thr Gly Thr Thr Thr
690                 695                 700

Gly Cys Thr Gly Cys Ala Gly Gly Ala Gly Ala Thr Gly Ala Ala Ala
705                 710                 715                 720

Thr Ala Cys Ala Ala Gly Thr Gly Gly Ala Thr Gly Thr Ala Thr
            725                 730                 735

Gly Gly Ala Gly Cys Ala Ala Gly Gly Thr Gly Cys Ala Gly Cys Gly
                740                 745                 750

Gly Cys Ala Ala Cys Cys Cys Thr Ala Thr Ala Cys Cys Ala Gly
        755                 760                 765

Gly Gly Thr Thr Gly Gly Ala Thr Gly Ala Ala Gly Thr Thr Cys Ala
770                 775                 780

Thr Thr Ala Ala Ala Gly Cys Ala Gly Cys Gly Gly Ala Cys Gly Ala
785                 790                 795                 800

Ala Ala Thr Gly Gly Ala Gly Gly Cys Cys Thr Cys Thr Gly Thr Gly
            805                 810                 815

Ala Ala Ala Gly Thr Gly Cys Ala Cys Cys Ala Ala Thr Cys Thr Ala
            820                 825                 830

Cys Thr Thr Cys Gly Cys Cys Gly Gly Cys Thr Cys Cys Ala Gly Cys
        835                 840                 845

Ala Gly Cys Cys Ala Ala Gly Gly Thr Gly Thr Thr Cys Thr Thr Gly
    850                 855                 860

Cys Thr Thr Cys Ala Thr Ala Cys Ala Gly Gly Cys Cys Thr Ala
865                 870                 875                 880

Thr Cys Gly Ala Gly Ala Ala Thr Ala Ala Ala Gly Thr Gly Cys Thr
            885                 890                 895

Gly Cys Cys Thr Gly Thr Gly Ala Ala Ala Gly Ala Gly Gly Ala Ala
                900                 905                 910

Gly Ala Gly Gly Ala Gly Thr Thr Cys Ala Ala Gly Ala Thr Cys Thr
    915                 920                 925

Cys Cys Gly Thr Gly Thr Thr Gly Gly Cys Thr Thr Cys Gly Cys
        930                 935                 940

Thr Gly Cys Gly Gly Thr Ala Gly Thr Ala Cys Cys Cys Gly Cys Gly
945                 950                 955                 960

Cys Ala Gly Thr Cys Thr Thr Cys Cys Thr Ala Thr Ala Ala Ala Cys
            965                 970                 975

Cys Thr Gly Gly Gly Gly Cys Ala Ala Ala Cys Ala Thr Ala Ala Cys
            980                 985                 990

Cys Cys Cys Gly Ala Ala Ala Ala Gly Ala Thr Thr Cys Gly Gly Ala
                995                 1000                1005

Gly Ala Ala Ala Thr Cys Gly Cys Thr Ala Cys Ala Gly Ala Gly
    1010                1015                1020

Gly Cys Ala Gly Gly Cys Gly Gly Gly Cys Cys Thr Ala Thr
    1025                1030                1035

Ala Thr Thr Cys Ala Gly Cys Thr Thr Cys Thr Cys Gly Cys
    1040                1045                1050
```

-continued

```
Ala Gly Ala Gly Gly Ala Gly Gly Thr Gly Ala Thr Gly Cys Gly
    1055                1060                1065

Gly Cys Thr Thr Thr Thr Gly Ala Thr Gly Ala Ala Gly Cys Ala
    1070                1075                1080

Gly Ala Ala Gly Thr Thr Gly Thr Gly Ala Gly Gly Thr Gly Gly
    1085                1090                1095

Cys Thr Gly Gly Cys Gly Gly Cys Cys Gly Ala Thr Gly Gly Ala
    1100                1105                1110

Thr Thr Gly Gly Ala Ala Ala Thr Thr Ala Ala Ala Ala Ala Ala
    1115                1120                1125

Gly Gly Ala Gly Gly Ala Gly Gly Ala Ala Thr Thr Ala Cys Ala
    1130                1135                1140

Ala Thr Gly Gly Ala Thr Thr Cys Thr Gly Cys Ala Gly Gly Gly
    1145                1150                1155

Ala Cys Thr Thr Ala Thr Gly Ala Ala Ala Ala Gly Ala Gly Ala
    1160                1165                1170

Thr Cys Gly Gly Ala Thr Ala Ala Ala Ala Gly Gly Gly Gly Ala
    1175                1180                1185

Gly Gly Ala Ala Ala Cys Gly Cys Ala Gly Cys Ala Gly Ala Cys
    1190                1195                1200

Gly Ala Ala Cys Thr Ala Ala Ala Cys Cys Cys Gly Ala Ala Ala
    1205                1210                1215

Gly Thr Cys Thr Gly Ala
    1220

<210> SEQ ID NO 6
<211> LENGTH: 405
<212> TYPE: PRT
<213> ORGANISM: Eimeria acervulina

<400> SEQUENCE: 6

Met Gly Gly Ser His His His His His Gly Met Ala Ser Met Thr
1               5                   10                  15

Gly Gly Met Gly Arg Asp Leu Tyr Asp Asp Asp Lys Asp Arg Trp
                20                  25                  30

Gly Ser Glu Leu Glu Met Gly Ala Ala Cys Met Lys Ser His Gly Ala
            35                  40                  45

Ala Thr Asp Ala Val Ala Pro Arg Arg Ser Thr Ala Glu Lys Ala Ala
        50                  55                  60

Asp Ala Ala Ala Ala Glu Glu His Ser His Lys Ala Gln Glu Ala
65                  70                  75                  80

Ala Glu Thr Ala Ala Ala Cys Ala Arg Arg Ala Cys Ala Glu Ala Ala
                85                  90                  95

Ser Leu Thr Gly Arg Gly Ser Gly Glu Ala Ala Ala Met Gln Gly Asp
                100                 105                 110

Pro Lys Val Asp Glu Thr Glu Glu Gln Gln Ile Thr Thr Thr Pro Ala
            115                 120                 125

Gln Thr His Ala Thr Glu Glu Pro Gln Ala Ser Ala Val Val Pro Leu
        130                 135                 140

Ser Asp Ala Asp Ala Gln Leu Leu Ala Ala Ala Glu Lys Gln Ala Ala
145                 150                 155                 160

Ala Lys Gln Gln Gln Gly Gly Ser Asn Thr Pro His Ala Tyr Leu Phe
                165                 170                 175

Tyr Ala Thr Glu Leu Asn Glu Gly Ser Leu Ile Met Gln Trp Thr Pro
            180                 185                 190
```

-continued

```
Thr Gln Met Ser Glu Glu Asp Met His Ala Lys Asn Leu Leu Leu
        195                 200                 205
Ala Ser Phe Thr Pro Ala Lys His Lys Thr Val Ser Lys Ser Lys Leu
        210                 215                 220
Thr Gln Asn Gly Gly Val Thr Cys Leu Leu Gln Glu Met Lys Tyr Lys
225                 230                 235                 240
Trp Asp Val Trp Ser Lys Val Gln Arg Gln Pro Tyr Tyr Gln Gly Trp
            245                 250                 255
Met Lys Phe Ile Lys Ala Ala Asp Glu Met Glu Ala Ser Val Lys Val
            260                 265                 270
His Gln Phe Thr Ser Pro Ala Pro Ala Ala Lys Val Phe Leu Leu His
        275                 280                 285
Thr Gly Pro Ile Glu Asn Lys Val Leu Pro Val Lys Glu Glu Glu Glu
    290                 295                 300
Phe Lys Ile Ser Val Phe Gly Phe Ala Ala Val Val Pro Ala Gln Ser
305                 310                 315                 320
Ser Tyr Lys Pro Gly Ala Asn Ile Thr Pro Lys Arg Phe Gly Glu Ile
            325                 330                 335
Ala Thr Glu Ala Gly Gly Ala Tyr Ile Gln Leu Ser Arg Arg Gly Gly
            340                 345                 350
Asp Ala Ala Phe Asp Glu Ala Glu Val Val Arg Trp Leu Ala Ala Asp
        355                 360                 365
Gly Leu Glu Ile Lys Lys Gly Gly Ile Thr Met Asp Ser Ala Gly
        370                 375                 380
Thr Tyr Glu Lys Arg Ser Asp Lys Lys Gly Gly Asn Ala Ala Asp Glu
385                 390                 395                 400
Leu Asn Pro Lys Val
            405
```

RECOMBINANT *EIMERIA MAXIMA* PROTEIN DELIVERED AS NANOPARTICLES

CROSS-REFERENCE

The present application claims priority to U.S. Provisional Patent Application Ser. No. 62/616,503 filed Jan. 12, 2018, the content of which is expressly incorporated herein by reference.

BACKGROUND OF THE INVENTION

Field of Invention

The subject matter disclosed herein provides immunogenic compositions containing nanoparticles and recombinant proteins capable of presenting all, or antigenic portions of, the *Eimeria maxima, Eimeria tenella*, and *Eimeria acervulina* IMP1 protein to a recipient, such as poultry. The immunogenic compositions are capable of inducing active immunity to, and control of, coccidiosis. Also provided are methodologies of using the immunogenic compositions for administration to poultry and other animals in the control of coccidiosis. In some instances, the IMP1 protein utilized in the immunogenic compositions presented herein is molecularly manipulated or combined with adjuvants to increase effectiveness.

Background

Avian coccidiosis is caused by multiple species of the genus *Eimeria* and imposes a great economic impact on poultry industry worldwide (Yin et al., Int. J. Parasitol. (2011) 41:813-6; Shirley et al., Avian Pathol. (2012) 41:111-21; Wu et al., Avian Dis. (2014)58:367-72). Although traditionally coccidiosis control was successful using prophylactic chemotherapy, increasing concerns with drug resistance, drug residue and the restricted governmental regulation on the use of drugs in agricultural animals hinder its application (Jeffers, J. K., in "Coccidia and Intestinal Coccidiomorphs", ed. P. Yvore (1989) pp 295-308; Lin et al., Gene (2011) 480:28-33). Immunization is an effective and cost-effective method of preventing infection and a live coccidiosis vaccine has been used for more than 50 years. However, there are inherent problems using live vaccines, including the necessity of introducing virulent coccidian into the poultry house and continual issues with inefficient and non-uniform vaccine delivery. Additionally, live coccidiosis vaccines consist of multiple different species of *Eimeria*, even different strains in some species of *Eimeria* spp. to account for the varied immunogenicity (Smith et al., Infect. Immun. (2002) 70:2472-9; Allen et al., Parasitol. Res. (2005) 97:179-85).

In recent years, induction of protective immunity using peptide vaccines has gained much interest with increasing technological advances in genetic engineering and protein expression (Shirley et al., supra). However, there remains an inability to elicit optimal levels of protective response against multiple coccidia species due to their weak immunogenicity and poor/undetermined cross-protection against different species. Thus, many challenges still remain before peptide antigens can be applied in commercial poultry production (Jang et al., Vaccine (2010) 28:2980-5; Shirley et al., supra; Liu et al., Parasit. Vectors (2014) 7:27; Xu et al., Korean J. Parasitol. (2013) 51:147-54).

Nanoparticles (NP) have been found to be readily taken up by antigen-presenting cells (APCs) and stimulate different arms of the immune system including helper T cells, with subsequent cytokine release (Marques et al., Front. Immunol., (2017) 8:239. NP smaller than 50 nm are efficiently internalized at mucosal surfaces (Howe et al., PLoS One (2014) 9:e86656; Howe & Konjufca, PLoS One (2014) 9:e114601), and when conjugated to a protein antigen, have the potential to induce both mucosal and systemic immune responses following mucosal administration (Howe & Konjufca, supra). In addition, NP-conjugated recombinant proteins have been used to elicit protective immunity against a number of parasitic diseases including malaria (Kumar et al., Vaccine (2015) 33:5064-71; Armada et al., Exp. Parasitol. (2013) 135:166-74; Kaba et al., PLoS One (2012) 7:e48304; Busic et al., Vaccine (2011) 29:8898-908; Kaba et al., J. Immunol. (2009) 183:7268-77), leishmaniasis (Badiee et al., Vaccine (2013) 31:735-49; Danesh-Bahreini et al., Int. J. Nanomed. (2011) 6:835-42; Ribeiro et al., Int. Immunopharmacol. (2017) 47:227-30; Agallou et al., PLoS Negl. Trop. Dis. (2017) 11:e0005311) and toxoplasmosis (Assolini et al., Parasitol. Res. (2017) 116:1603-15; Ducournau et al., Future Microbol. (2017) 12:393-405; Chahal et al., Proc. Nat'l. Acad. Sci. USA (2016) 113:E4133-42).

Several recombinant *Eimeria* antigens have been shown to confer protective immunity against avian coccidiosis (see, e.g., Blake & Tomley, Trends Parasitol. (2013) 30:12-9), which has generally been measured by a decrease in parasite development (oocyst excretion) at relatively low challenge doses. Of the recombinant *Eimeria* antigens showing protective efficacy, the *E. maxima* immune-mapped protein 1 (EmaxIMP1) appeared to be a promising candidate for inclusion in a subunit vaccine against coccidiosis (Blake et al., PLoS Pathog. (2011) 7:e1001279), however, use of this protein as a subunit vaccine has not been shown to be effective against high-challenge doses that affect weight gain (clinical efficacy).

Our preliminary studies using recombinant EmaxIMP1 delivered by intramuscular, intranasal, or oral inoculation has failed to provide significant protection against clinical effects of *E. maxima* challenge (unpublished observations). The purpose of this study was to determine whether delivering recombinant EmaxIMP1 as a conjugate to nanoparticles could improve the level of protection as measured by weight gain against *E. maxima* infection. The surprising results provided herein are that, despite the failure of other routes of inoculation with recombinant IMP1, the rIMP1-NP conjugates induced protection in treated poultry.

SUMMARY OF THE INVENTION

Provided herein are several embodiments of the disclosed invention. One such embodiment is an immunogenic composition, comprising a recombinant protein of SEQ ID NO: 2, a recombinant protein comprising amino acid residues 40-415 of SEQ ID NO: 2, a recombinant protein having at least 95% identity to SEQ ID NO: 2, or a recombinant protein comprising an antigenic portion of SEQ ID NO: 2, where the recombinant protein is conjugated to a nanoparticle, and where the nanoparticle/recombinant protein is capable of inducing an immune response to the recombinant in a recipient. Such compositions can comprise an adjuvant. Immunogenic compositions of the present invention can be formulated for nasal or oral delivery. In preferred embodiments, the recipient is poultry, such as a chicken or turkey.

Also provided herein is an embodiment that is a method of protecting a recipient against coccidiosis, where an immunogenic composition described above is administered to the recipient in an amount effective to induce a protective immune response to an *Eimeria* species, such as *E. maxima, E. tenella*, or *E. acervulina*. In preferred embodiments, the recipient is poultry, such as a chicken or turkey. In some embodiments of this method, immunogenic composition is administered to the recipient at a dose comprising at least 10 µg of recombinant protein. In practicing this methodology, the immunogenic composition can be administered nasally or orally.

An additional embodiment of the present invention provides a method in which an immunogenic composition produced according to the process by the steps of: (a) culturing a recombinant host cell transformed with SEQ ID NO: 1, a DNA sequence encoding a protein having at least 95% identity to SEQ ID NO: 2, a DNA sequence encoding a protein comprising amino acid residues 40-415 of SEQ ID NO: 2, or a DNA sequence encoding a protein comprising an antigenic portion of SEQ ID NO:2; (b) expressing the protein encoded by SEQ ID NO:1, a DNA sequence encoding a protein having at least 95% identity to SEQ ID NO:2, a DNA sequence encoding a protein comprising amino acid residues 40-415 of SEQ ID NO: 2, or a DNA sequence encoding a protein comprising an antigenic portion of SEQ ID NO:2; (c) purifying the expressed protein; and (d) conjugating the purified protein to a nanoparticle. In some embodiments, this process can also include the incorporation of an adjuvant. In an exemplary embodiment, the host cell used is an *Escherichia coli* cell.

Further provided herein, is an immunogenic composition, comprising a recombinant protein selected from the group comprising: [1] a recombinant protein of SEQ ID NO: 4, [2] a recombinant protein comprising amino acid residues 42-438 of SEQ ID NO: 4, [3] a recombinant protein having at least 95% identity to SEQ ID NO: 4, and [4] a recombinant protein comprising an antigenic portion of SEQ ID NO: 4; wherein said recombinant protein is conjugated to a nanoparticle.

In an additional embodiment provided herein, an immunogenic composition is disclosed, comprising a recombinant protein selected from the group comprising: [1] a recombinant protein of SEQ ID NO: 6, [2] a recombinant protein comprising amino acid residues 38-405 of SEQ ID NO: 6, [3] a recombinant protein having at least 95% identity to SEQ ID NO: 6, and [4] a recombinant protein comprising an antigenic portion of SEQ ID NO: 6; wherein said recombinant protein is conjugated to a nanoparticle.

Further provided herein are immunogenic compositions produced according to the process comprising the steps of: 1) culturing a recombinant host cell transformed with an exogenous DNA, wherein the exogenous DNA is selected from the group consisting of SEQ ID NO: 3, SEQ ID NO: 5, a DNA sequence encoding a protein having at least 95% identity to SEQ ID NO: 4, a DNA sequence encoding a protein having at least 95% identity to SEQ ID NO: 6, a DNA sequence encoding a protein comprising amino acid residues 42-438 of SEQ ID NO: 4, a DNA sequence encoding a protein comprising amino acid residues 38-405 of SEQ ID NO: 6, a DNA sequence encoding a protein comprising an antigenic portion of SEQ ID NO: 4, and a DNA sequence encoding a protein comprising an antigenic portion of SEQ ID NO: 6; 2) expressing the protein encoded by the exogenous DNA; 3) purifying the protein produced in the expressing step to yield a purified protein; and 4) conjugating the purified protein to a nanoparticle.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

Figure 1:
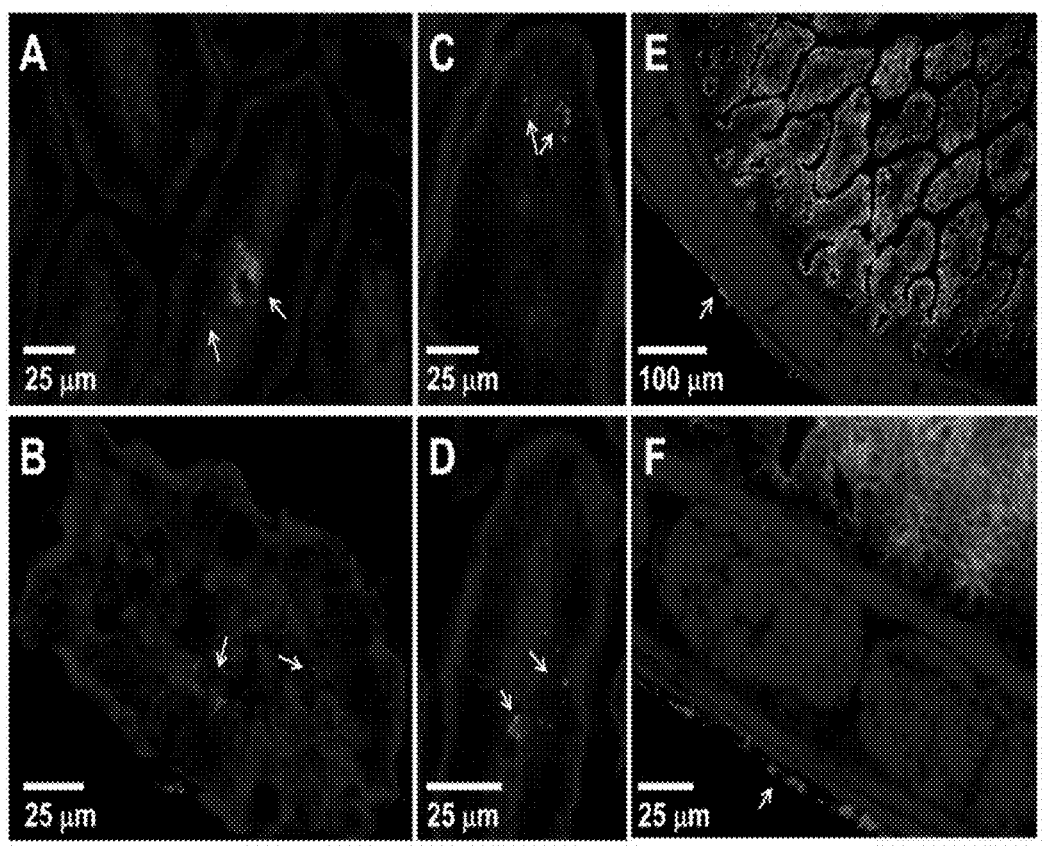
FIG. 1. Per-orally administered nanoparticles (NP) conjugated to recombinant *E. maxima* IMP1 (EmaxIMP1) or non-recombinant (NR) protein derived from *E. coli* that harbors an empty plasmid reach the lamina propria and serosa of the chicken small intestine within 1-6 h. (Panels A-D) 20 nm NP (red, arrows) within the lamina propria of the intestinal villi. (Panels A, C) NP-NR, (Panels B, D) NP-EmaxIMP1, (Panels E,F) 20 nm NP-EmaxIMP1 in the serosa of the small intestine (arrows) 6 h after per os administration. Tissue cryosections were stained with actin-binding Phalloidin-Alexa350 (Panels A-F, blue) and anti-E-cadherin antibodies (Panels E, F, green).

*maxima* IMP1 antigen delivered in conjunction with nanoparticles (Floor Pens). Shown are the differences in feed conversion ratio (FCR) over infection period. NINC, non-immunized, non-*E. maxima* challenge controls; NIC, non-immunized, *E. maxima* challenge controls; EmaxIMP1, recombinant *E. maxima* IMP1 protein linked to nanoparticles; NR, non-recombinant protein linked to nanoparticles. Asterisks reflect significant differences between treatments as estimated by two-way t-test: *, FCR significantly greater than NINC controls (P<0.10); **, FCR significantly less than NR control (P<0.10). Data shown is an average of 2 independent vaccination trials, with experimental treatments conducted in triplicate.

DETAILED DESCRIPTION OF THE INVENTION

The purpose of this study was to determine if conjugating a recombinant *E. maxima* protein, namely EmaxIMP1, into 20 nm polystyrene nanoparticles (NP) could improve the level of protective immunity against *E. maxima* challenge infection. Previously, we had failed to induce protection in poultry by using this purified recombinant protein in a saline carrier or expressed in a live-cell *E. coli* form, regardless of route of administration.

As described herein, recombinant EmaxIMP1 was expressed in *E. coli* as a poly-His fusion protein, purified by NiNTA chromatography, and conjugated to 20 nm polystyrene NP (NP-EmaxIMP1). NP-EMaxIMP1 or control non-recombinant protein (NP-NR) were delivered per os to newly-hatched broiler chicks with subsequent booster immunizations at 3 and 21 days of age. In battery cage studies (n=8), chickens immunized with NP-EMaxIMP1 displayed complete protection as measured by weight gain (WG) against *E. maxima* challenge compared to chickens immunized with NP-NR. WG in the NP-EMaxIMP1-immunized groups was identical to WG in chickens that were not infected with *E. maxima* infected chickens.

Thus, we present herein immunogenic compositions comprising nanoparticle-conjugated recombinant IMP1 and methodologies of using them to induce immune protection in a recipient (e.g., poultry such as chickens and turkeys).

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The term "about" is defined as plus or minus ten percent of a recited value. For example, about 1.0 g means 0.9 g to 1.1 g and all values within that range, whether specifically stated or not.

The term "IMP1" refers to the proteins defined herein as SEQ ID NO: 2, SEQ ID NO: 4, or SEQ ID NO: 6. The definition also includes a protein having amino acid residues 40-415 of SEQ ID NO: 2, a protein having amino acid residues 42-438 of SEQ ID NO: 4, or a protein having amino acid residues 38-405 of SEQ ID NO: 6. The term also includes proteins encoded by the DNA of SEQ ID NO: 1, SEQ ID NO: 3, SEQ ID NO: 5, (or any version of these nucleic acids with base substitutions that result in a protein with an amino acid sequence identical to SEQ ID NO: 2, SEQ ID NO: 4, SEQ ID NO: 6 or the above referenced sub-sequences). These terms also refer to modified versions of these SEQ ID NOs, such as those comprising regulatory nucleic acids, or proteins (and the nucleic acids encoding them) containing additional moieties allowing for purification (e.g., His tag), or immunogenicity-enhancement. Where indicated, these terms can also include antigenic sub-portions of the provided protein sequence(s).

As used herein, the term "poultry" refers to one bird, or a group of birds, of any type of domesticated birds typically kept for egg and/or meat production. For example, poultry includes chickens, ducks, turkeys, geese, bantams, quail, pheasant, pigeons, or the like, preferably commercially important poultry such as chickens, ducks, geese and turkeys.

The terms "isolated", "purified", or "biologically pure" as used herein, refer to material that is substantially, or essentially, free from components that normally accompany the referenced material in its native state.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii)

transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

In practicing some embodiments of the invention disclosed herein, it can be useful to modify the genomic DNA of a recombinant strain of a host cell producing the immunogenic protein of the immunogenic compositions (e.g., IMP1 protein). In preferred embodiments, such a host cell is *E. coli*. Such modification can involve deletion of all or a portion of a target gene, including but not limited to the open reading frame of a target locus, transcriptional regulators such as promoters of a target locus, and any other regulatory nucleic acid sequences positioned 5' or 3' from the open reading frame. Such deletional mutations can be achieved using any technique known to those of skill in the art. Mutational, insertional, and deletional variants of the disclosed nucleotide sequences and genes can be readily prepared by methods which are well known to those skilled in the art. It is well within the skill of a person trained in this art to make mutational, insertional, and deletional mutations which are equivalent in function to the specific ones disclosed herein.

Where a recombinant nucleic acid is intended for expression, cloning, or replication of a particular sequence, DNA constructs prepared for introduction into a prokaryotic or eukaryotic host will typically comprise a replication system (i.e. vector) recognized by the host, including the intended DNA fragment encoding a desired polypeptide, and can also include transcription and translational initiation regulatory sequences operably linked to the polypeptide-encoding segment. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Nucleic acids and proteins of the present invention can also encompass sequences with high identity to the specifically disclosed sequences. Identity can be 50%-100%. In some instances, such identity is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using any algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Immunogenic Compositions

An immunogenic composition is defined herein as a biological agent which is capable of providing a protective response in an animal to which the immunogenic composition has been delivered and is incapable of causing severe disease. Administration of the immunogenic compositions result in increased immunity to a disease; the immunogenic compositions stimulate antibody production, cellular immunity, or both against the pathogen(s) causing the disease. Immunity is defined herein as the induction of a significantly higher level of protection in a population of recipients, such as poultry, against mortality and clinical symptoms after receipt of an immunogenic composition compared to an untreated group. In particular, the immunogenic composition(s) according to the invention can: (a) protect a large proportion of treated animals against the occurrence of clinical symptoms of the disease and mortality, or; (b) result in a significant decrease in clinical symptoms of the disease and mortality.

The immunogenic composition(s) of the invention herein, regardless of other components included, comprise a recombinant IMP1 protein from an *Eimeria* species, including *E. maxima, E. tenella*, and *E. acervulina*. IMP1 proteins of the present invention can comprise the entirety of SEQ ID NO: 2, a protein comprising amino acid residues 40-415 of SEQ ID NO: 2, or antigenic portions thereof. IMP1 proteins of the present invention can also include those with 90%, 91%, 92%, 93%, 94%, 95%, 96%, 97%, 98%, 99%, or higher identity to the protein of SEQ ID NO: 2, SEQ ID NO: 4, or SEQ ID NO: 6. IMP1 proteins of the present invention can also comprise a protein comprising amino acid residues 40-415 of SEQ ID NO: 2, a protein comprising amino acid residues 42-438 of SEQ ID NO: 4, or a protein comprising amino acid residues 38-405 of SEQ ID NO: 6 or proteins having 90%, 91%, 92%, 93%, 94%, 95%, 96%, 97%, 98%, 99%, or higher identity to these portions of SEQ ID NO: 2, SEQ ID NO: 4, SEQ ID NO: 6. In preferred embodiments, the immunogenic compositions of the present invention comprise a recombinant IMP1 protein from *E. maxima, E. tenella*, or *E. acervulina* conjugated to a nanoparticle.

The immunogenically effective amounts of immunogenic compositions disclosed herein can vary based upon multiple parameters. In general, however, effective amounts per dosage unit can be about 10-200 μg recombinant IMP1 protein, about 20-150 μg recombinant IMP1 protein, or about 50-100 μg recombinant IMP1 protein. An individual dose can contain 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250 or more μg of recombinant IMP1 protein per dose. These amounts can also include antigenic portions of the full length IMP1 protein. In preferred embodiments, the immunogenic compositions of the present invention comprise a recombinant IMP1 protein from *E. maxima* conjugated to a nanoparticle.

One, two, or more dosage units can be utilized in practicing the methodologies of the present invention. If two dosage units are selected, then vaccination at about day 1 post-hatch and again at about one week to two weeks of age is preferred. A dosage unit can readily be modified to fit a desired volume or mass by one of skill in the art. Regardless of the dosage unit parameters, immunogenic compositions disclosed herein can be administered in an amount effective to produce an immune response to the presented antigen (e.g., IMP1 protein). An "immunogenically effective amount" or "effective amount" of an immunogenic composition as used herein, is an amount of the composition that provides sufficient levels of antigenic protein to produce a desired result, such as induction of, or increase in, production of antibody specific to the antigen, protection against coccidiosis, as evidenced by a reduction in gastrointestinal lesions, increased weight gain, and decreased oocyst shedding and other indicators of reduction in pathogenesis. Amounts of immunogenic compositions capable of inducing such effects are referred to as an effective amount, or immunogenically effective amount, of the immunogenic compositions.

Dosage levels of active ingredients (e.g., IMP1 protein) in immunogenic compositions disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. As used herein, the term "minimal dose" or "minimal effective dose" refers to a dose that demonstrates the absence of, or minimal presence of, toxicity to the recipient, but still results in producing a desired result (e.g., protective immunity). Minimal effective doses, or minimum immunizing doses, of the recombinant immunogenic compositions provided herein can include about 10-200 μg recombinant IMP1 protein, about 20-150 μg recombinant IMP1 protein, or about 50-100 μg recombinant IMP1 protein. The minimal effective doses can also be any dose within the range of 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250 or more μg of recombinant IMP1 protein per dose. These amounts can also include antigenic portions of the full length IMP1 protein. Determination of a minimal dose is well within the capabilities of one skilled in the art.

Nanoparticles

Nanoparticles (NPs) have unique properties that may be useful in a diverse range of applications, and consequently they have attracted significant interest, particularly in the field of vaccines and drugs. In a biological medium, NPs can interact with proteins due to their size and large surface-to-mass ratio. Of particular importance is the adsorption or conjugation of proteins on the nanoparticle surface. The formation of nanoparticle-protein complexes is commonly referred to as the nanoparticle-protein corona (NP-PC) and the NP-PC can influence the biological reactivity of the NP and conjugated protein (Saptarshi et al., J. Nanobiotech., (2013) 11:26).

For immunogenic compositions of the present invention, any suitable nanoparticle can be utilized. Preferably, a nanoparticle is of a material that does not cause detrimental side effects in the target (e.g., poultry). Preferred nanoparticles have a size between 5-200 nm, including but not limited to approximately 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 nanometers. Preferably, a nanoparticle useful in the present invention is between 10-100 nm and most preferably between 10-50 nm.

Nanoparticles of the present invention can be made of any relevant material known or developed in the art. Non-limiting examples of nanoparticle material include synthetic polymers (polystyrene, poly(d,l-lactide-co-glycolide), poly (d,l-lactic-coglycolic acid), poly(g-glutamic acid), polyethylene glycol), natural polymers (latex, pullulan, alginate, inulin, chitosan), copolymers, and inorganic substances (gold, $TiO_2$, $SiO_2$, ZnO, $CaPO_4$, multiwall carbon nanotubes, superparamagnetic iron-oxide). The choice of nanoparticle material to utilize for developing and using immunogenic compositions of the present invention is within the capabilities of one skilled in the art.

Formulations

In some instances, immunogenic compositions of the present invention also contain or comprise one or more adjuvants, which includes any material included in the immunogenic composition formulation that enhances an immune response in the recipient that is induced by the immunogenic composition. In some instances, such adjuvants can include proteins other components included with the antigenic protein (e.g., IMP1 protein). Non-limiting examples of such adjuvants can include engineered proteins in which the (e.g., IMP1 protein) is expressed as a fusion protein operably linked with immunity-enhancing moieties. Other adjuvants can be included as an extra component of the immunogenic compositions, and include such categories as aluminum salts (alum), oil emulsions, saponins, immune-stimulating complexes (ISCOMs), liposomes, microparticles, nonionic block copolymers, derivatized polysaccharides, cytokines, and a wide variety of bacterial derivatives. Such adjuvants can include, for example, ISA 71, IMS 1313, immunostimulating complex, AB5 toxins (e.g., cholera toxin), *E. coli* heat labile toxin, monophosphoryl lipid A, flagellin, c-di-GMP, inflammatory cytokines, chemokines, definsins, chitosan, phytochemicals, and combinations of these. Any relevant adjuvant known in the art can be utilized in practicing the inventions disclosed herein. Factors influencing the selection of an adjuvant include animal species, specific pathogen, antigen, route of immunization, and type of immunity needed and can be readily determined by one of skill in the art.

Immunogenic compositions of the present invention can also comprise in addition to the recombinant protein component and nanoparticles. Carriers utilized in practicing the immunogenic compositions provided herein can be any known in the art and can be liquid, solid, semi-solid, or gel. The type of formulation can be modified depending on the route of administration of the antigen. For oral administration, the immunogenic compositions of the present invention can be applied to carriers such as pellets, tablets, kibbles, chewables, powders and beads, as well as specific materials such as microcrystalline cellulose (MCC), plant-based products and soil-based products (e.g., clays). Preferably, carriers are non-toxic to the recipient. In some instances the immunogenic compositions of the present invention, with or without carriers, can be presented to a recipient for ingestion via suspension in drinking water. One of skill in the art is readily able to choose such carriers for application to recipient animals such as poultry.

Administration Methodologies

The present disclosure provides compositions for introducing a recombinant immunogenic composition containing, at a minimum, a recombinant *E. maxima* IMP1 protein, or antigenic fragments thereof, into targets (e.g., poultry). Thus, the compositions provided herein can be utilized to induce immunity or resistance to *Eimeria* species (e.g., *E. maxima, E. tenella, E. acervulina*) and more generally, the disease coccidiosis in targets to which the antigen is provided. In preferred embodiments, the recombinant proteins of the present invention are conjugated to nanoparticles.

An immunogenic composition of the present invention is preferably administered via ingestion or intranasally in an amount which is effective to protect the recipient (e.g., poultry). Administration of immunogenic compositions of the present invention can also be applied in ovo, prior to hatching, via any technique known in the art. Typically, in ovo application is performed during incubation. Application of an immunogenic composition to a subject can result in the development of immunity to the IMP1 protein, preferably development of an effective immune response that results in the decrease or removal of clinical symptoms. Application of the immunogenic compositions of the present invention can be provided at multiple times or in a single dosage. Application of the immunogenic compositions provided herein to poultry can occur for the first time about day 1 post-hatch or any time thereafter. Application can be performed before, during or after the development of *Eimeria*-caused coccidiosis, including coccidiosis caused by *E. tenella, E. maxima, E. acervulina*, and other *Eimeria* species.

Having generally described this invention, the same will be better understood by reference to certain specific examples, which are included herein to further illustrate the invention and are not intended to limit the scope of the invention as defined by the claims.

EXAMPLES

Example 1

Preparation of Recombinant *E. maxima* IMP1 Conjugated to Nanoparticles (NP)

Recombinant EmaxIMP1 was expressed as a polyHis fusion protein in *Escherichia coli* BL21 (from the pTrcHis expression vector, Invitrogen, Carlsbad, Calif.) or *E. coli* Top10 (from the pBadHis expression vector, Invitrogen) as described elsewhere (Jenkins et al., Vet. Parasitol., (2015) 211:146-52), and purified by NiNTA affinity chromatography following manufacturer's instructions (Invitrogen). The purity of EmaxIMP1 in NiNTA eluates was confirmed by SDS-PAGE followed by staining with colloidal Coomassie blue staining; the concentration of EMaxIMP1 protein was determine by BCA assay (Pierce Chemical Co., Dallas, Tex.). NP-EmaxIMP1 were prepared using a procedure described elsewhere (Howe et al., PLoS one (2014) 9:e86656) In brief, conjugation of EmaxIMP1 to NP was carried out by first mixing 200 ul carboxylate-modified fluorescent polystyrene NP with 800 μL of 100 mM PBS solution, and then adding 2.0 mg recombinant EmaxIMP1. The mixture was incubated at room temperature for 15 minutes followed by the addition of 8.0 mg of 1-ethyl-3-(3-dimethylaminopropyl) carbodiimide-hydrochloride (EDAC-HCl). The reaction mixture was incubated for 2 hours at room temperature with regular agitation. The resulting particle dispersion was then dialyzed using a Float-A-Lyzer® membrane (100 kDa cutoff) for 3 days against 100 mM PBS (pH 7.4) that was changed daily. The resulting protein-conjugated NPs were diluted in PBS to achieve a 20% NP solution. An equivalent amount of non-recombinant (NR) protein was conjugated to NP in a separate tube. NR protein was obtained by applying NiNTA purification to a protein extract of *E. coli* harboring non-recombinant pTrcHisA plasmid (i.e. plasmid not containing the EmaxIMP1 gene sequence). After NP conjugation, the mixture was dialyzed against 0.01 M PBS (pH 7.4) for 3 days at 4° C. using a Float-A-Lyzer membrane (100 kDa cutoff) (Spectrum Labs, Inc., Rancho Dominguez, Calif.) with 2 changes of PBS each day. After dialysis, the conjugated NP-EmaxIMP1 and NP-NR were transferred to a 1.5 ml microcentrifuge tube and diluted with PBS to achieve a 20% NP solution. The conjugation of EMaxIMP1 to NP was confirmed by dot blot analysis using rabbit anti-EMaxIMP1 sera followed by FITC-conjugated anti-rabbit IgG (Sigma-Aldrich, St. Louis, Mo.) as described elsewhere (Jenkins et al., 2015, supra).

Example 2

Tissue Localization of Conjugated NP-EmaxIMP1 and NP-NR Following Per Os Administration Newly-hatched male broiler chicks (Longeneckers Hatchery, Elizabethtown, Pa.) were inoculated per os with 100 μl of NP-EmaxIMP1 or NP-NR. After 1 h or 6 h, the chicks (n=3/timepoint and treatment) were euthanized for necropsy to remove the small intestine, bursa, and spleen. For the small intestine, a 2 cm section flanking 1 cm on either side of the Meckels diverticulum was excised, and the intestinal lumen was gently filled with Tissue-Tek O.C.T Compound (Sakura, Torrance, Calif.) using a syringe containing a blunt-end needle. The intestine was then placed in a Tissue-Tek vinyl Cryomold (25 mm×20 mm×5 mm, Sakura) filled about half-way with OCT. The tissue-containing Cryomold was placed on a block of dry ice and OCT was immediately added to the top of the Cryomold. After the block was completely frozen, the Cryomold was placed in a separate dry ice container. A similar procedure was followed for bursa and spleen with some modifications. For bursa, a longitudinal cut was made to divide the tissue in half. One half of the bursa was left intact, while individual plicae were separated using a scapel; all sections were then placed in a single Cryomold containing OCT compound and processed as described above. The spleen was excised, excess fat removed, and the entire tissue was transferred to a single Cryomold containing OCT compound and processed as described above.

Figure 2:
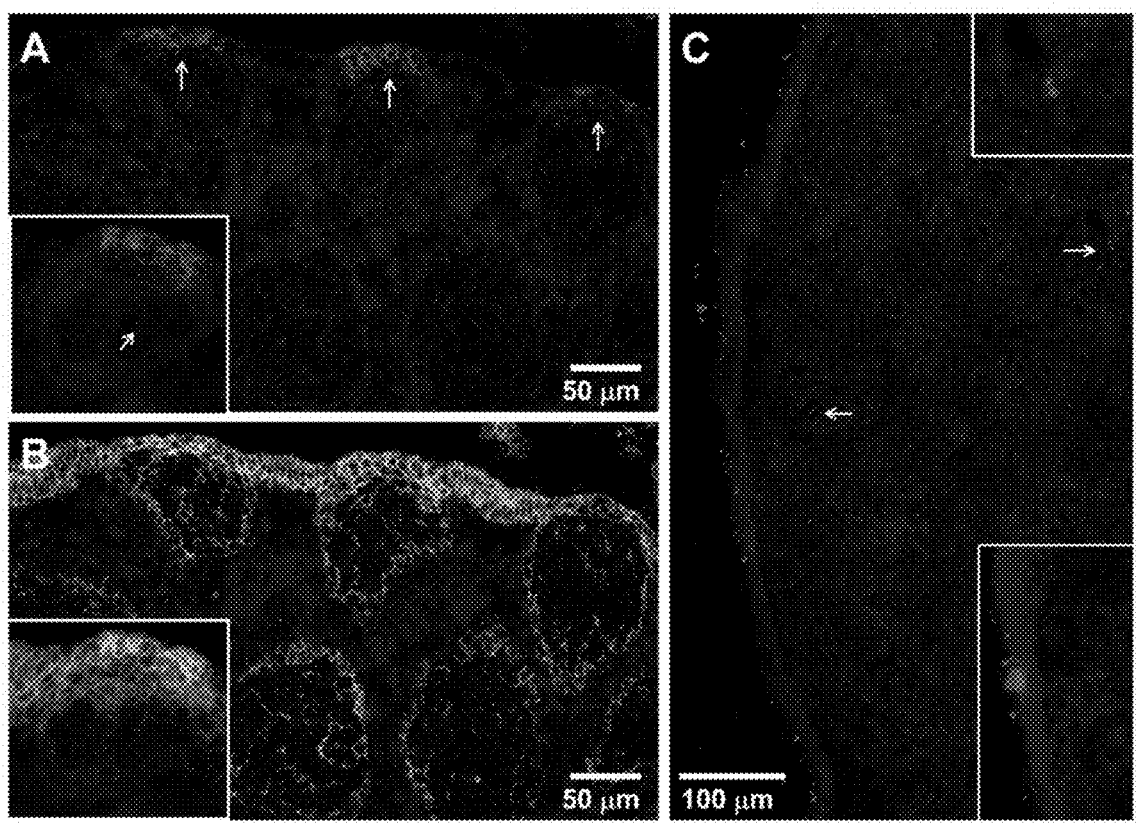
FIG. 2. Per-orally administered NP conjugated to *E. maxima* IMP1 (EmaxIMP1) or non-recombinant (NR) reach the bursa of Fabricius and the spleen of chickens within 1-6 h. (A, B) 20 nm NP-NR (red) internalized by the follicle-associated epithelium (FAE) of the bursa 6 h following the PO administration. (C) 20 nm NP-EmaxIMP1 in the spleen 6 h after PO administration. Insets: larger magnification images showing NP. Tissue cryosections were stained with actin-binding Phalloidin-Alexa350 (A-C, blue) and anti-E-cadherin antibodies (B, green).

20 nm NP-IMP-1 and NP-NR were observed in the lamina propria and serosa of the small intestine within 1 h (data not shown) and 6 h after per os administration (FIG. 1). At 6 h after per os administration, both NP-EmaxIMP1 and NP-NR were observed in the epithelium and lamina propria of the small intestinal villi in chickens inoculated with either NP-NR (FIG. 1, panels A, C) or NP-IMP1 (FIG. 1, panels B,D). An intense fluorescence signal emitted from accumulated NPs was observed in the serosa of the small intestine chickens at 6 h post-inoculation (FIG. 1, panels E,F) indicating that NP has crossed the mucosal-lumen interface and reached the circulation. Moreover, NP reached the bursa of Fabricius and were internalized by the E-cadherin expressing follicle-associated epithelium (FAE) within 1 h of per os administration (data not shown). However, at 6 h, larger amount of NPs were found within FAE, as well as in the sub-epithelial regions of the bursal follicles (FIG. 2, panels A, B). In addition to mucosal tissues, NP also reached the spleen within 1 h (data not shown) and 6 h post-inoculation (FIG. 2, panel C). NP were observed not only in the capsule, but also within the splenic tissue (FIG. 2, panel C, insets). In all tissues accumulated "clumps" of NP can easily be observed (FIGS. 1 and 2), however, single NPs are more difficult to image due to their small size and low fluorescence signal. Overall, these data indicate that 20 nm NP are very efficiently internalized at mucosal surfaces and reach the deeper tissues within 1-6 h.

Example 3

Battery Cage Studies

Newly hatched (<6 hr-old) broiler chicks (n=3 replicates/treatment, 4 chicks/replicate; male Hubbard/Ross HR708, Longeneckers Hatchery) were inoculated per os with 40 µl NP-EmaxIMP1 or NP-NR. On days 3 and 21, all vaccinated chicks received an oral booster immunization with 40 µl of the identical NP immunogen used in the primary immunization. All chicks, including non-immunized controls, were housed by treatment groups in separate cages of a Petersime starter unit (Petersime, Gettysburg, Ohio), and transferred at 2 wk of age to individual cages of Petersime finisher units at 3 cages/treatment and 4 chickens/cage. Chicks were provided water and standard poultry ration (crumbles, 24% protein) ad libitum. At 4 wk of age, all immunized chickens, and a control group of non-immunized chickens (NIC), were challenged with 750 E. maxima (APU1) oocysts. This challenge dose was based on dose titration studies designed to achieve a 20-25% reduction in weight gain in non-immunized challenged (NIC) controls. Another group of non-immunized chickens were not challenged with E. maxima oocysts to serve as non-challenged controls (NINC). Body weights of all chickens were measured on day of challenge infection and 6 days post-challenge in order to calculate weight gain during the peak infection period. Feed conversion ratio (FCR) was also calculated for each replicate by dividing average feed consumption by average weight gain during the infection period. A total of 8 separate vaccination-challenge battery cage studies were conducted to evaluate the protective effect of NP-EMaxIMP1 against E. maxima infection.

Figure 3:
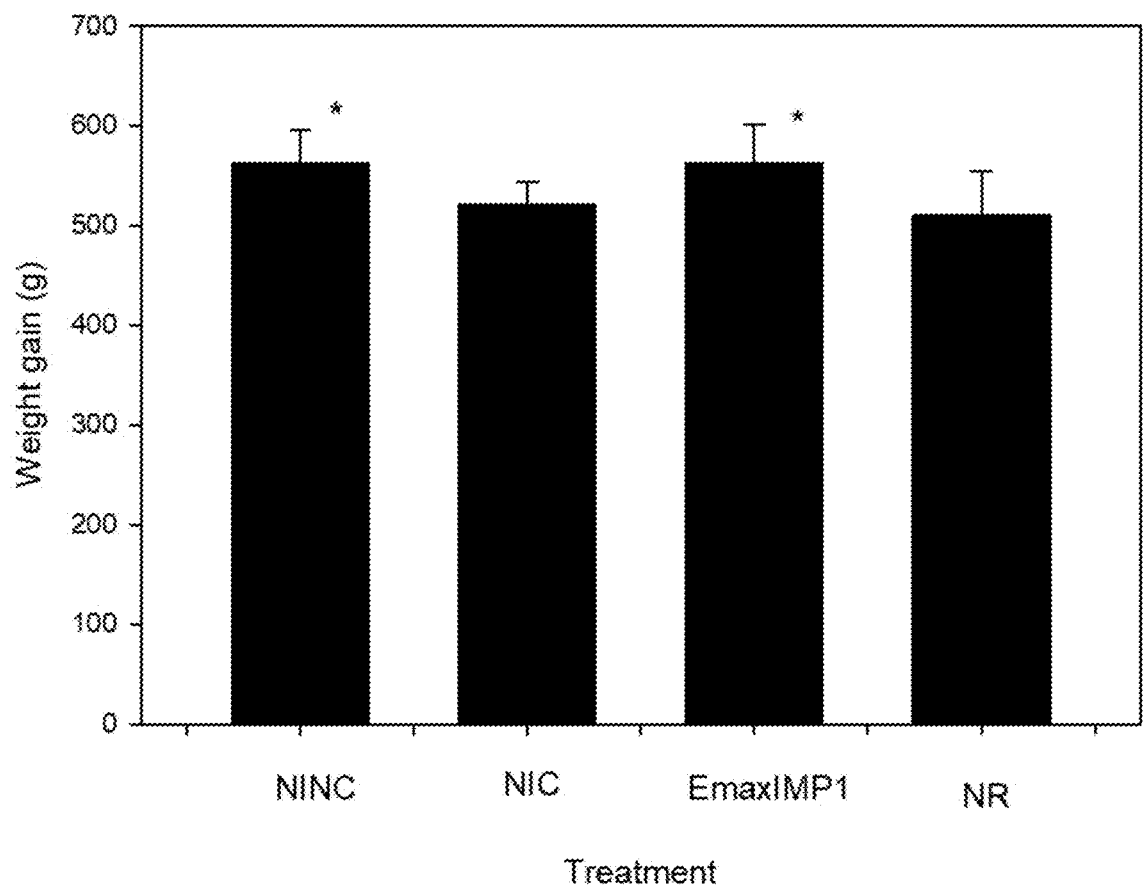
FIG. 3. Protection of broiler chickens against *Eimeria maxima* challenge infection by immunization with recombinant *E. maxima* IMP1 antigen delivered in conjunction with nanoparticles (Battery Cages). Shown are the differences in weight gain (WG) over the infection period. NINC, non-immunized, non-*E. maxima* challenge controls; NIC, non-immunized, *E. maxima* challenge controls; EmaxIMP1, recombinant *E. maxima* IMP1 protein linked to nanoparticles; NR, non-recombinant protein linked to nanoparticles. Asterisks reflect significant differences between treatments as estimated by ANOVA: *, WG significantly greater than NR control (P<0.05). Data represents an average of 8 independent vaccination trials, with experimental treatments conducted in triplicate.

A significant increase (P<0.05) in average weight gain (WG) during 6 d post-E. maxima challenge was observed in NP-EmaxIMP1-inoculated chickens relative to NP-NR-inoculated controls (FIG. 3). Weight gain in the NP-EmaxIMP1 inoculated chickens was equal (P>0.05) to that observed in non-E. maxima challenged controls (NINC) (FIG. 3). Although FCR values were measurably increased (less efficient feed conversion efficiency) in NP-NR-inoculated chickens relative to NP-EmaxIMP1-inoculated chickens, no significant differences in FCR between these groups was observed (data not shown)

Example 4

Floor Pen Studies

Newly hatched (<6 hr old) broiler chicks (n=3 replicates/treatment, 10 chicks/replicate; male Hubbard/Ross HR708, Longeneckers Hatchery) were inoculated per os with 40 µl NP-EmaxIMP1 or NP-NR. On days 3 and 21, all vaccinated chicks received an oral booster immunization with 40 µl of the identical NP-antigen used in the primary immunization. All chicks in each treatment group, including non-immunized controls, were assigned to 3 separate pens (10 chicks/pen), each pen measuring 1.5 m×0.5 m×0.75 m (length×width×height). The bottom of each pen contained 5-10 cm in depth wood shavings, and each pen was raised about 0.5 m above a concrete floor. Chicks were provided water and standard poultry ration (crumbles, 24% protein) poultry feed ad libitum. At 4 weeks of age, all immunized chickens, and a control group of non-immunized chickens (NIC), were challenged with 750 E. maxima (APU1) oocysts. Another group of non-immunized chickens were not challenged with E. maxima oocysts to serve as non-challenged controls (NINC). Body weights of all chickens were measured on day of E. maxima challenge and 6 days post-challenge in order to calculate weight gain during the peak infection period. FCR was also calculated for each replicate by dividing average feed consumption by average weight gain during the infection period. A total of 2 separate vaccination-challenge floor pen studies were conducted to evaluate the protective effect of NP-EMaxIMP1 against E. maxima infection. All animal studies were conducted under an animal protocol approved by the Beltsville Animal Care and Use Committee.

Figure 4:
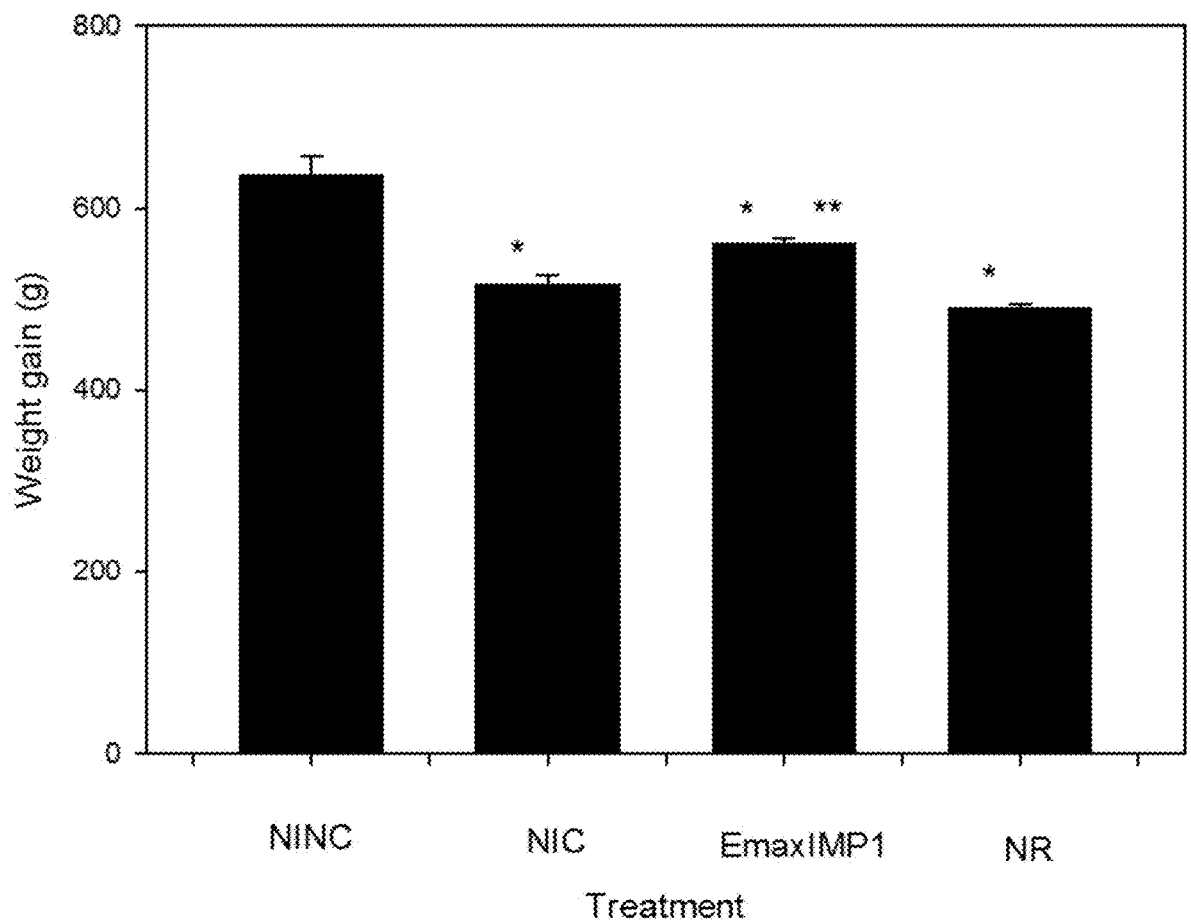
FIG. 4. Protection of broiler chickens against *E. maxima* challenge infection by immunization with recombinant *E. maxima* IMP1 antigen delivered in conjunction with nanoparticles (Floor Pens). Shown are the differences in weight gain over the infection period. NINC, non-immunized, non-*E. maxima* challenge controls; NIC, non-immunized, *E. maxima* challenge controls; EmaxIMP1, recombinant *E. maxima* IMP1 protein linked to nanoparticles; NR, non-recombinant protein linked to nanoparticles. Asterisks reflect significant differences between treatments as estimated by two-way t-test: *, WG significantly less than NINC controls (P<0.10); **, WG significantly greater than NR control (P<0.10). Data represents an average of 2 independent vaccination trials, with experimental treatments conducted in triplicate.
Figure 5:
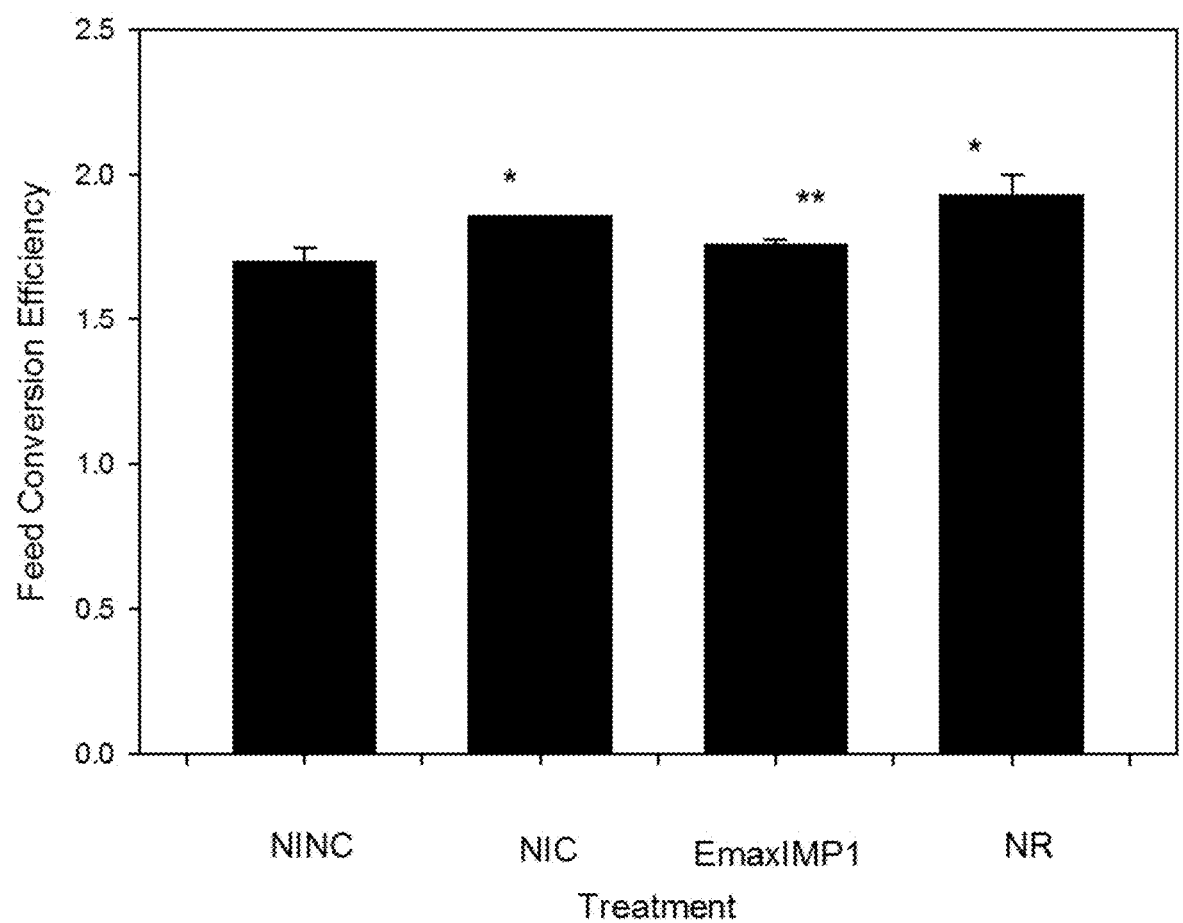
FIG. 5. Protection of broiler chickens against *E. maxima* challenge infection by immunization with recombinant *E.*

Partial protection against E. maxima challenge infection was observed in chickens inoculated with NP-EmaxIMP1. NP-EmaxIMP1-inoculated chickens displayed a significant increase (P<0.10) in WG compared to NP-NR or NIC chickens (FIG. 4). However, this WG was less (P<0.10) than that observed in NINC controls (FIG. 4). Protection as measured by feed conversion efficiency displayed a pattern similar to WG. FCR in NP-EmaxIMP1-inoculated chickens was significantly lower (P<0.10) than in NP-NR-inoculated chickens (FIG. 5). FCR in NP-EmaxIMP1-inoculated chickens displayed no significant difference relative to NINC controls (P>0.10) (FIG. 5).

Example 5

Parasites and Statistical Analyses

Coccidiosis challenge infection utilized *Eimeria maxima* (APU1) oocysts that had been propagated in susceptible chickens every 3-4 months for 10 years after initial isolation (Fetterer et al., J. Parasitol., (2003) 89:553-64). The purity of *E. maxima* oocysts was confirmed by ITS1-PCR using procedures described elsewhere (Jenkins et al., Avian Dis., (2006) 50:632-5).

For battery cage studies, mean weight gain (WG) and FCR from each of 8 independent studies were compared between groups using one-way ANOVA followed by Tukey-Kramer Multiple Comparisons Test (InStat Software Package, GraphPad Software, LaJolla, Calif.). Differences between means were considered significant at P<0.05.

Example 6

Unsuccessful Vaccination with EmaxIMP1 in the Absence of Nanoparticles

Recombinant EmaxIMP1 was expressed as a polyHis fusion protein in *Escherichia coli* and purified by NiNTA affinity chromatography. The purified rEmaxIMP1 was used to immunize newly-hatched chickens by a variety of routes including oral or nasal inoculation or by intramuscular injection. All chicks received a booster immunization at 3 and 21 days of age with the same amount of purified rEmaxIMP1. Other chicks were immunized by oral inoculation with live *E. coli* expressing rEmaxIMP1 followed by 2 booster oral inoculation with the same recombinant *E. coli*. All chickens were challenged with *E. maxima* oocysts at 4 weeks of age (1 week after the last booster immunization) to determine if immunization had any protective effect against coccidiosis infection.

No significant protection (P>0.05) as measured by weight gain was observed in any chickens immunized with either aqueous EmaxIMP1 or as live *E. coli* expressing EmaxIMP1. For instance, chickens immunized per os with aqueous EmaxIMP1 displayed weight gains that were similar to non-immunized controls (NIC) or to chickens immunized with non-recombinant *E. coli* protein. This weight gain was much lower than the non-*E. maxima* challenge controls (NINC). Likewise, chickens orally inoculated with *E. coli* expressing EmaxIMP1 displayed weight gain that was similar to chickens given non-recombinant *E. coli* or non-immunized *E. maxima* challenge controls (NIC) and less than non-challenge controls. Lastly, chickens receiving rEmaxIMP1 by nasal inoculation either in aqueous or live *E.* coli form both displayed weight gain that was similar to non-immunized controls (NIC) and much less than non-*E. maxima* challenge controls.

Thus, immunization with rEmaxIMP1 in either aqueous form or as live *E. coli* delivered by either oral or nasal inoculation or intramuscular injection displayed no significant protection (P>0.05) against *E. maxima* challenge infection relative to non-recombinant controls (NR) or to non-immunized control chickens that were challenged with *E. maxima* oocysts.

While the invention has been described with reference to details of the illustrated embodiments, these details are not intended to limit the scope of the invention as defined in the appended claims. The embodiments of the invention in which exclusive property or privilege is claimed is defined as follows:

What is claimed is:

1. An immunogenic composition, comprising a recombinant protein selected from the group consisting of: a recombinant protein comprising the amino acid sequence of SEQ ID NO: 2, a recombinant protein comprising amino acid residues 40-415 of SEQ ID NO: 2, a recombinant protein having at least 95% identity to SEQ ID NO: 2, and a recombinant protein comprising an antigenic portion of the protein comprising the amino acid sequence of SEQ ID NO: 2; wherein said recombinant protein is conjugated to a nanoparticle, and wherein said immunogenic composition is capable of inducing an immune response to said recombinant protein in a recipient.

2. The immunogenic composition of claim 1, further comprising an adjuvant.

3. The immunogenic composition of claim 1, wherein the immunogenic composition is formulated for nasal delivery.

4. The immunogenic composition of claim 1, wherein the immunogenic composition is formulated for oral delivery.

5. An immunogenic composition produced according to the process comprising the steps of:

a. culturing a recombinant host cell transformed with an exogenous DNA, wherein the exogenous DNA is selected from the group consisting of a nucleic acid having the DNA sequence of SEQ ID NO: 1, a DNA sequence encoding a protein having at least 95% identity to SEQ ID NO: 2, a DNA sequence encoding a protein comprising amino acid residues 40-415 of SEQ ID NO: 2, or a DNA sequence encoding a protein comprising an antigenic portion of SEQ ID NO:2;

b. expressing the protein encoded by the exogenous DNA;

c. purifying the protein produced in the expressing step to yield a purified protein; and d. conjugating the purified protein to a nanoparticle.

6. The immunogenic composition of claim 5, wherein said process further comprises the step of incorporating an adjuvant.

7. The immunogenic composition of claim 5, wherein the host cell is an *Escherichia coli* cell.

* * * * *